US010085825B2

(12) United States Patent
Benfield et al.

(10) Patent No.: US 10,085,825 B2
(45) Date of Patent: Oct. 2, 2018

(54) WATER CONTROL VALVE

(71) Applicant: Kavo Dental Technologies, LLC, Charlotte, NC (US)

(72) Inventors: Thomas Mark Benfield, York, SC (US); Lindsey Michael Howe, Belmont, NC (US)

(73) Assignee: KAVO DENTAL TECHNOLOGIES, LLC, Charlotte, NC (US)

( * ) Notice: Subject to any disclaimer, the term of this patent is extended or adjusted under 35 U.S.C. 154(b) by 121 days.

(21) Appl. No.: 15/165,767

(22) Filed: May 26, 2016

(65) Prior Publication Data

US 2017/0343121 A1    Nov. 30, 2017

(51) Int. Cl.
    *A61C 17/00*    (2006.01)
    *A61C 17/02*    (2006.01)
    *F16K 31/122*    (2006.01)

(52) U.S. Cl.
    CPC ........ *A61C 17/0217* (2013.01); *F16K 31/122* (2013.01)

(58) Field of Classification Search
    CPC ............... A61C 17/0217; F16K 31/122; F16K 31/1221; F16K 31/1223
    See application file for complete search history.

(56) References Cited

U.S. PATENT DOCUMENTS

| | | | |
|---|---|---|---|
| 3,497,395 A | 2/1970 | Kohen | |
| 3,667,502 A * | 6/1972 | Otto | F15B 11/15 137/624.14 |
| 4,944,676 A | 7/1990 | Hu | |
| 5,201,899 A | 4/1993 | Austin, Jr. et al. | |
| 5,901,749 A * | 5/1999 | Watson | F16K 11/048 137/625.27 |
| 6,209,565 B1 * | 4/2001 | Hughes | F16K 31/1221 137/107 |
| 6,968,855 B1 | 11/2005 | Kemmerer et al. | |
| 2006/0118168 A1 | 6/2006 | Cheung | |

FOREIGN PATENT DOCUMENTS

EP    0387598 A1    9/1990

OTHER PUBLICATIONS

International Search Report and Written Opinion for Application No. PCT/US2017/03318 dated Aug. 17, 2017 (12 pages).
International Preliminary Report on Patentability for Application No. PCT/US2017/033188 dated Jul. 9, 2018 (23 pages).

* cited by examiner

*Primary Examiner* — Eric Keasel
(74) *Attorney, Agent, or Firm* — Michael Best & Friedrich LLP

(57) ABSTRACT

A water control valve includes a valve body defining a valve body internal cavity, a first air inlet passageway in communication with the valve body internal cavity, a first water outlet passageway in communication with the valve body internal cavity, and a water inlet passageway. The water control valve further includes a valve cartridge removably coupled to the valve body. The valve cartridge is sized to fit at least partially within the valve body internal cavity. The valve cartridge defines a second air inlet passageway and a second water outlet passageway. The first air inlet passageway is aligned with the second air inlet passageway and the first water outlet passageway is aligned with the second water outlet passageway when the valve cartridge is coupled to the valve body.

20 Claims, 7 Drawing Sheets

WATER CONTROL VALVE

BACKGROUND

Embodiments relate to water control valves. Certain embodiments relate to water control valves for use in dental equipment and systems.

Water control valves often suffer from degradation of valve components due to the quality of water from city municipalities, underground wells, etc. This degradation may damage, and in some cases, disable the valves. Water control valves also often suffer from excessive noise due to venting or leaking of air, as well as from difficulty in quickly and easily replacing or repairing components.

SUMMARY

One embodiment provides a water control valve having a valve body defining a valve body internal cavity, a first air inlet passageway in communication with the valve body internal cavity, a first water outlet passageway in communication with the valve body internal cavity, and a water inlet passageway. The water control valve further includes a valve cartridge removably coupled to the valve body. The valve cartridge is sized to fit at least partially within the valve body internal cavity. The valve cartridge defines a second air inlet passageway and a second water outlet passageway. The first air inlet passageway is aligned with the second air inlet passageway and the first water outlet passageway is aligned with the second water outlet passageway when the valve cartridge is coupled to the valve body.

Another embodiment provides a water control valve having a valve body having a wall. The valve body defines a valve body internal cavity and an air inlet passageway in communication with the valve body internal cavity, the air inlet passageway extending through the wall. The water control valve also includes a valve cartridge removably coupled to the valve body. The valve cartridge is sized to fit at least partially within the valve body internal cavity. The water control valve also includes a venting system for venting air out of the water control valve, the venting system including a plurality of grooves disposed in the wall and in communication with the air inlet passageway.

Other embodiments and aspects will become apparent by consideration of the detailed description and accompanying drawings.

DETAILED DESCRIPTION

Figure 1:
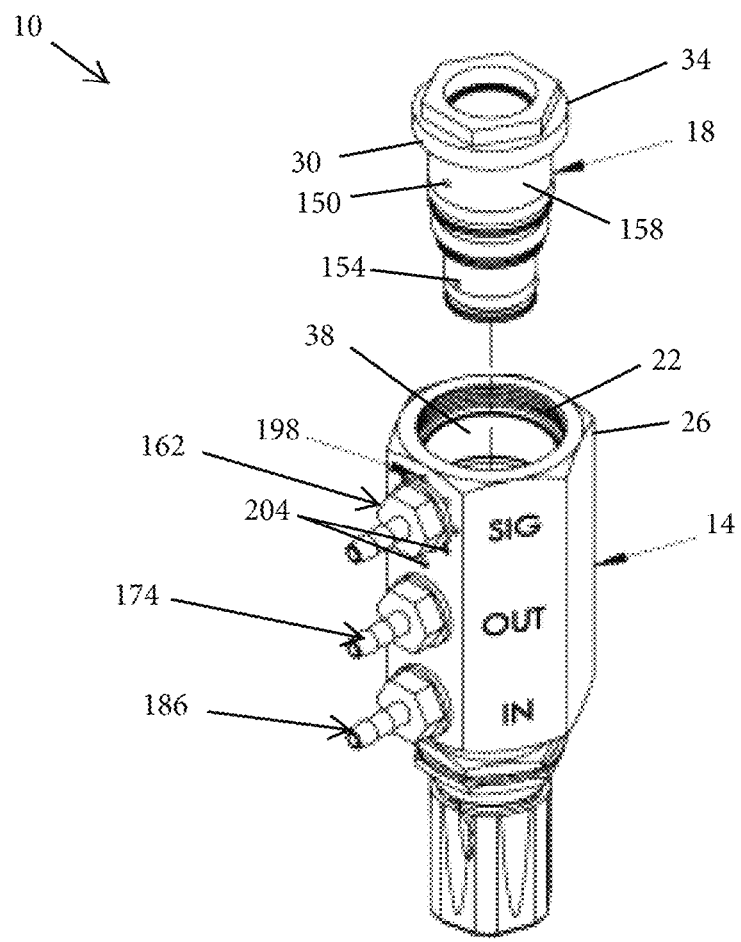
FIG. 1 is a perspective, partially exploded view of a water control valve according to one embodiment, illustrating a valve body and a valve cartridge that is removably coupled to the valve body.

Before any embodiments are explained in detail, it is to be understood that the invention is not limited in its application to the details of construction and the arrangement of components set forth in the following description or illustrated in the following drawings. The invention is capable of other embodiments and of being practiced or of being carried out in various ways. In addition, a device or structure disclosed as being configured in a certain way can be configured in at least that way, but can also be configured in ways that are not listed. In addition, in the following description, it can be seen that various features are grouped together in various embodiments for the purpose of streamlining the disclosure. This does not mean that the claimed embodiments require more features than are expressly recited in each claim. It only means that inventive subject matter may be encompassed in fewer than all features of a single disclosed embodiment or combinations (whether full or partial) of disclosed embodiments as set forth in the written description.

FIGS. 1-4 illustrate a water control valve 10 that controls a flow of water. In the example illustrated, water control valve 10 is intended for use in dental equipment and systems (for example, in a dental operatory). However, the water control valve 10 may be used in a variety of different medical or other desired equipment and systems to control a flow of water.

As illustrated in FIGS. 1-4, the water control valve 10 includes a valve body 14 and a valve cartridge 18 that is removably coupled to the valve body 14. In the illustrated construction, the valve body 14 includes a set of internal threads 22 at a top end 26 of the valve body 14, and the valve cartridge 18 includes a set of external threads 30 (illustrated schematically) at a top end 34 of the valve cartridge 18. The internal threads 22 and the external threads 30 are used to quickly and easily couple and de-couple the valve cartridge 18 to and from the valve body 14 as desired. Other constructions include different structures to removably couple the valve cartridge 18 to the valve body 14. For example, in some constructions a bayonet-type connection (e.g., quarter turn), or keyed connection, is provided instead of the threaded connection illustrated in FIGS. 1-4.

With continued reference to FIGS. 1-4, the valve body 14 includes a valve body internal cavity 38. When the valve cartridge 18 is coupled to the valve body 14, at least a portion (e.g., substantially all or all) of the valve cartridge 18 is disposed within the valve body internal cavity 38. In the illustrated construction, the internal threads 22 are disposed within the valve body internal cavity 38, and substantially all of the valve cartridge 18 is disposed within the valve body internal cavity 38 when the valve cartridge 18 is coupled to the valve body 14.

Figure 2:
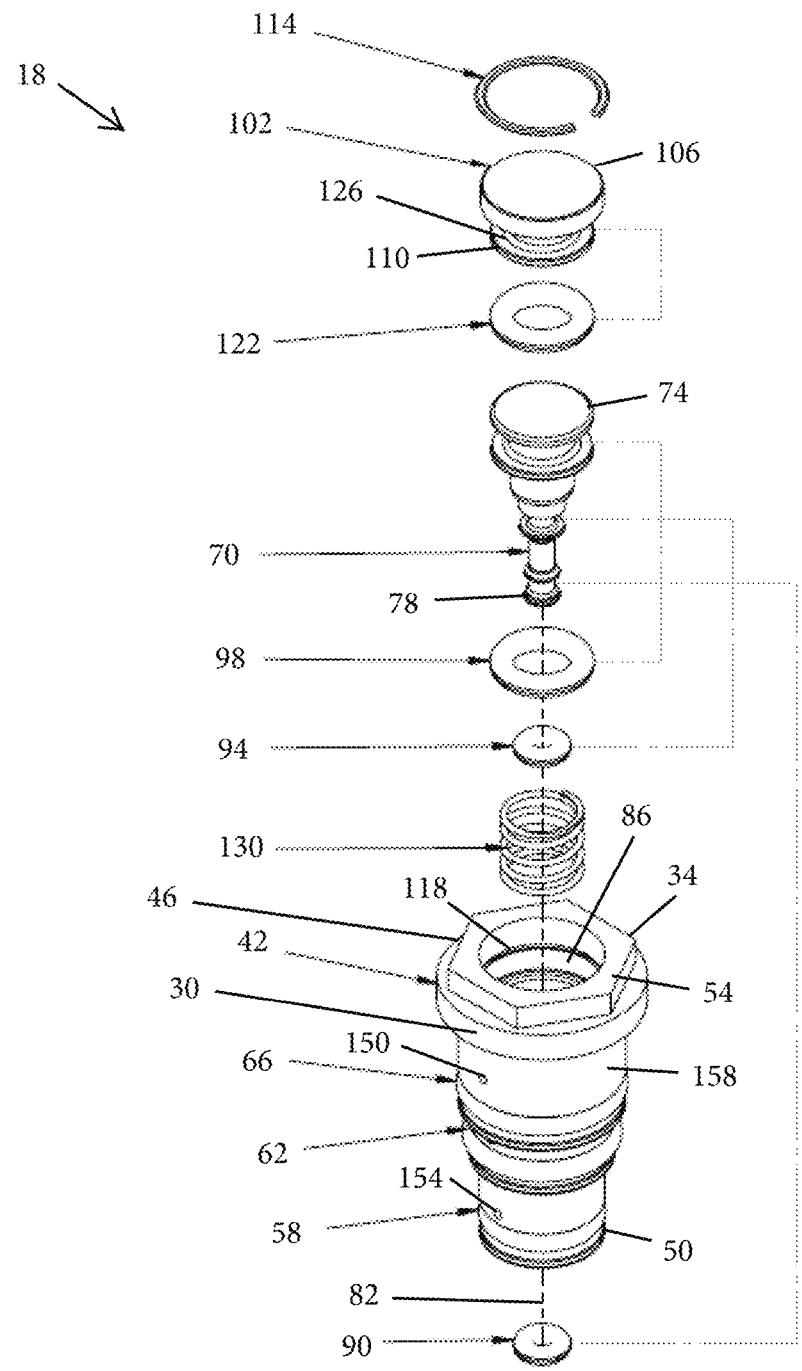
FIG. 2 is a perspective, exploded view of the valve cartridge.

With reference to FIG. 2, the valve cartridge 18 includes a main cartridge body 42 having a top end 46 and a bottom end 50. The main cartridge body 42 generally tapers in outside diameter moving from the top end 46 toward the bottom end 50, such that the bottom end 50 has a smaller outside diameter than the top end 46. In the illustrated construction, the main cartridge body 42 has a stepped taper, although other constructions include different shapes and tapers than that illustrated. In some constructions the main cartridge body 42 does not taper (e.g., is a generally cylindrical body having a constant diameter). In the illustrated construction, the tapered shape of the main cartridge body 42 facilitates insertion and removal of the valve cartridge 18 into and out of the valve body 14.

With continued reference to FIG. 2, the main cartridge body 42 further includes a fastening projection 54 at the top end 46 of the main cartridge body 42. The fastening projection 54 is used to couple the valve cartridge 18 to the valve body 14. In the illustrated construction the fastening projection 54 is a hexagonal projection that is gripped by a socket wrench, pliers, or other tool and turned to tighten or loosen the connection between the internal and external threads 22, 30 to couple and de-couple the valve cartridge 18 to and from the valve body 14.

With continued reference to FIG. 2, the valve cartridge 18 further includes a first sealing member 58, a second sealing member 62, and a third sealing member 66. Each of the first, second, and third sealing members 58, 62, 66 is coupled to an exterior of the main cartridge body 42. In the illustrated construction the first, second, and third sealing members 58, 62, 66 are O-rings positioned at locations along the main cartridge body 42 where the main cartridge body 42 steps down in outside diameter, although other constructions include different sealing members, as well as different locations or numbers of sealing members than that illustrated.

With continued reference to FIG. 2, the valve cartridge 18 further includes a piston 70 having a top end 74 and a bottom end 78. In use, the piston 70 moves along an axis 82 within a main cartridge body internal cavity 86. As illustrated in FIG. 2, the piston 70 generally tapers in outside diameter moving from the top end 74 toward the bottom end 78, such that the bottom end 78 has a smaller outside diameter than the top end 74.

The valve cartridge 18 further includes a fourth sealing member 90, a fifth sealing member 94, and a sixth sealing member 98. Each of the fourth, fifth, and sixth sealing members 90, 94, 98 is coupled to an exterior of the piston 70. In the illustrated construction the fourth, fifth, and sixth sealing members 90, 94, 98 are O-rings positioned at locations along the piston 70 where the piston 70 changes in diameter, although other constructions include different sealing members, as well as different locations or numbers of sealing members than that illustrated.

Figure 5:
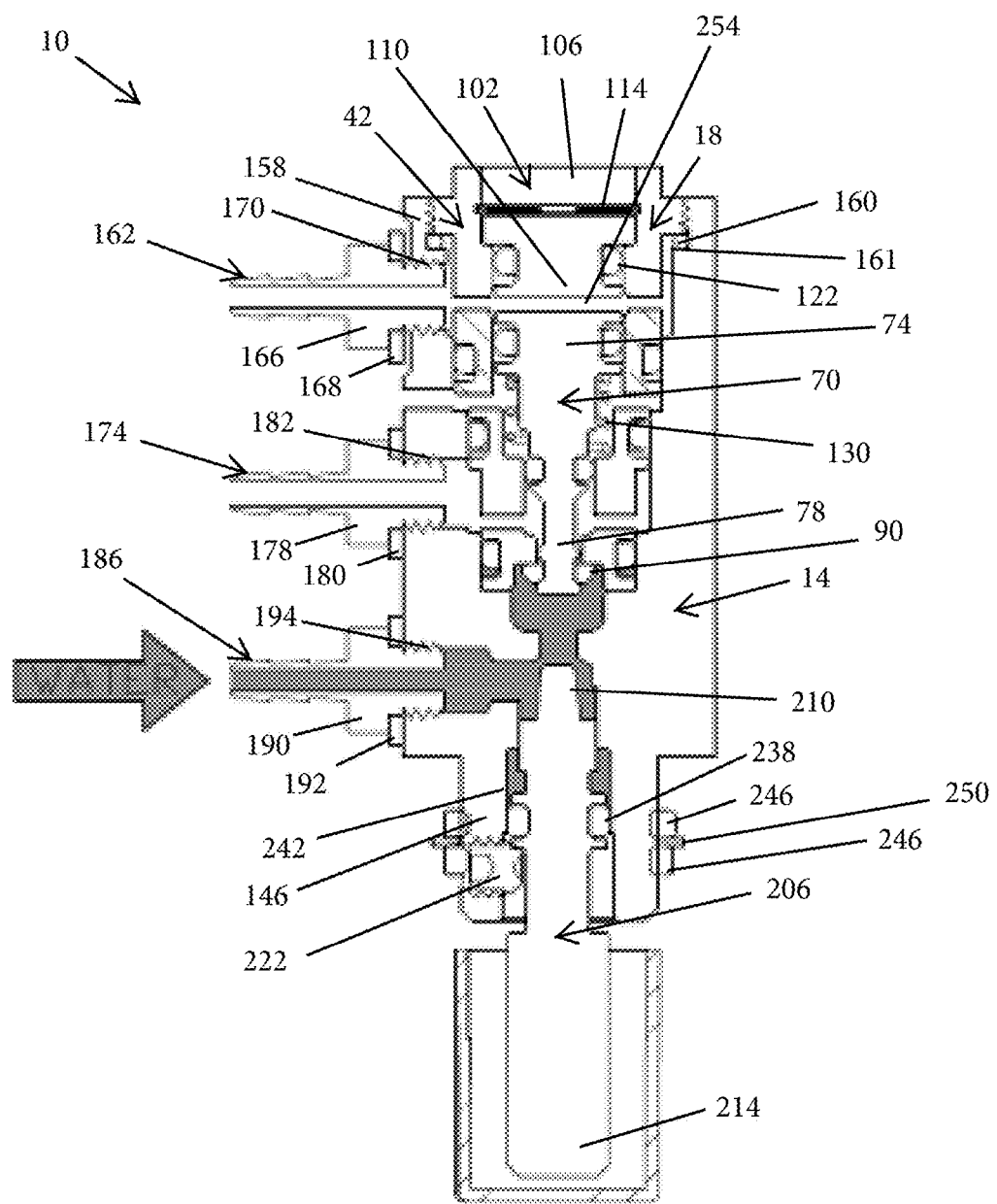
FIG. 5 is a schematic, cross-sectional view of the water control valve, illustrating a static condition.

With continued reference to FIG. 2, the valve cartridge 18 further includes a plug 102 having a top end 106 and a bottom end 110. In use the plug 102 remains stationary along the axis 82 within the main cartridge body internal cavity 86. For example, as illustrated in FIG. 2, as well as in FIG. 5, the valve cartridge 18 includes a retaining ring 114, and the main cartridge body 42 includes a retaining recess 118. The retaining ring 114 contacts and surrounds the plug 102 adjacent the top end 106 (e.g., frictionally), and is at least partially inserted into the retaining recess 118 to help hold the plug 102 in place in a stationary manner (as seen in FIG. 5).

With continued reference to FIG. 2, the valve cartridge 18 further includes a seventh sealing member 122 that is coupled to an exterior of the plug 102 and is disposed within a groove 126 along the plug 102. In the illustrated construction, the seventh sealing member 122 is an O-ring, although other constructions include different sealing members, as well as different locations or numbers of sealing members than that illustrated.

Figure 6:
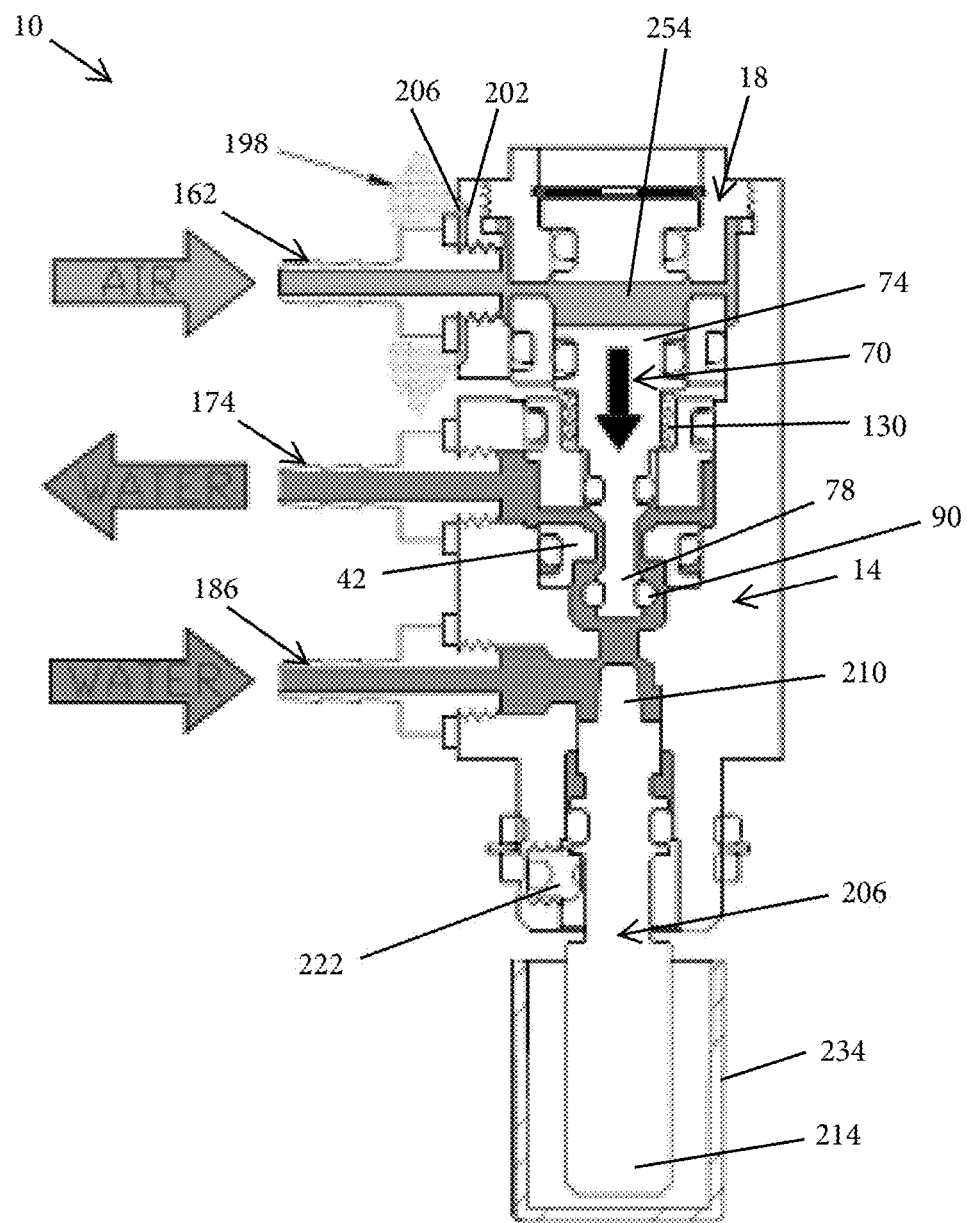
FIG. 6 is a schematic, cross-sectional view of the water control valve, illustrating an opening condition.
Figure 7:
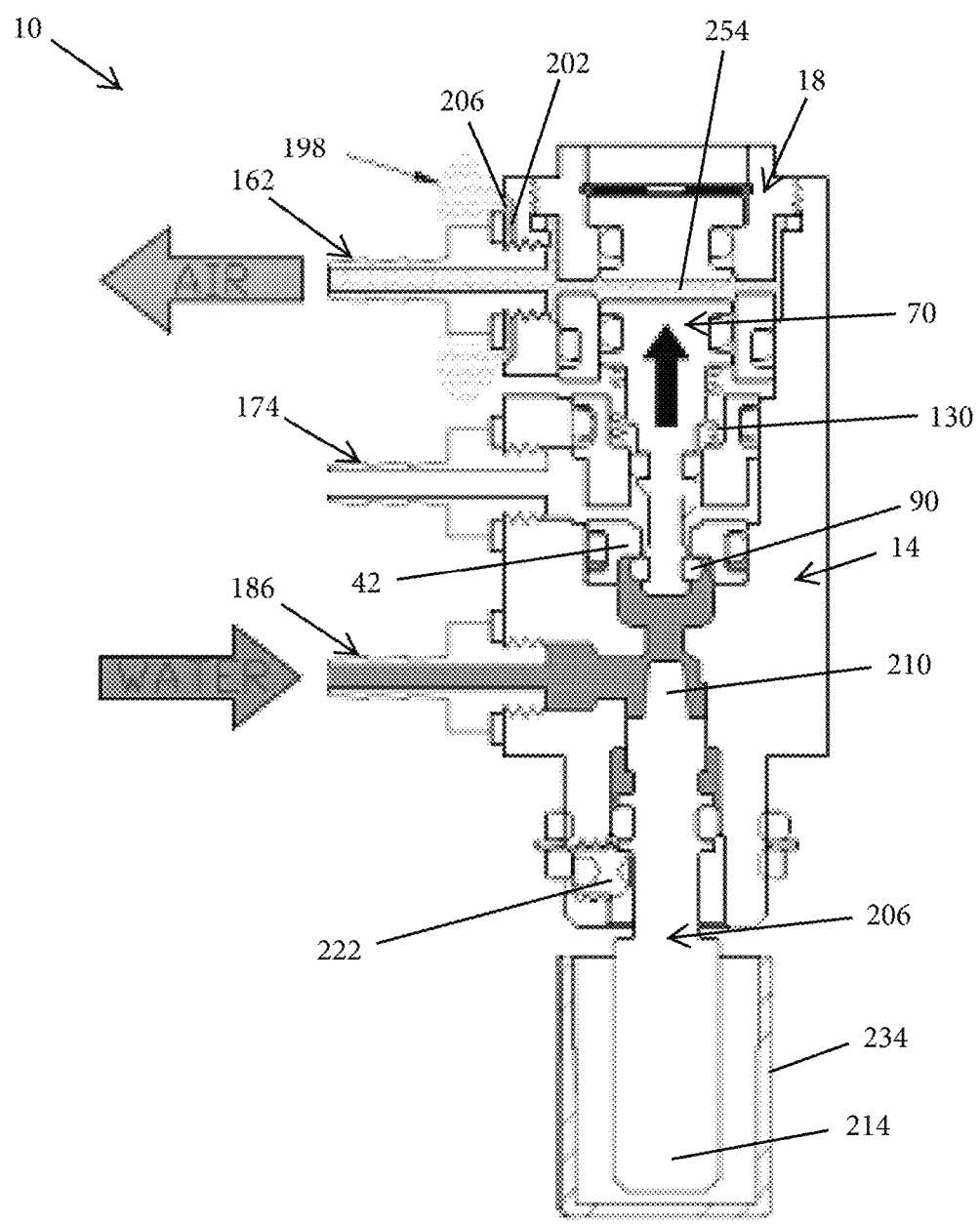
FIG. 7 is a schematic, cross-sectional view of the water control valve, illustrating a closing condition.

With continued reference to FIG. 2, the valve cartridge 18 further includes a biasing member 130. In the illustrated construction the biasing member 130 is a single compression spring, although constructions include different numbers and/or types of biasing members (e.g., tension spring, torsion spring, etc.). The biasing member 130 is disposed within the main cartridge body internal cavity 86, and is in contact with the piston 70 to control and guide movement of the piston 70 within the main cartridge body internal cavity 86 (as seen in FIGS. 5-7).

Figure 3:
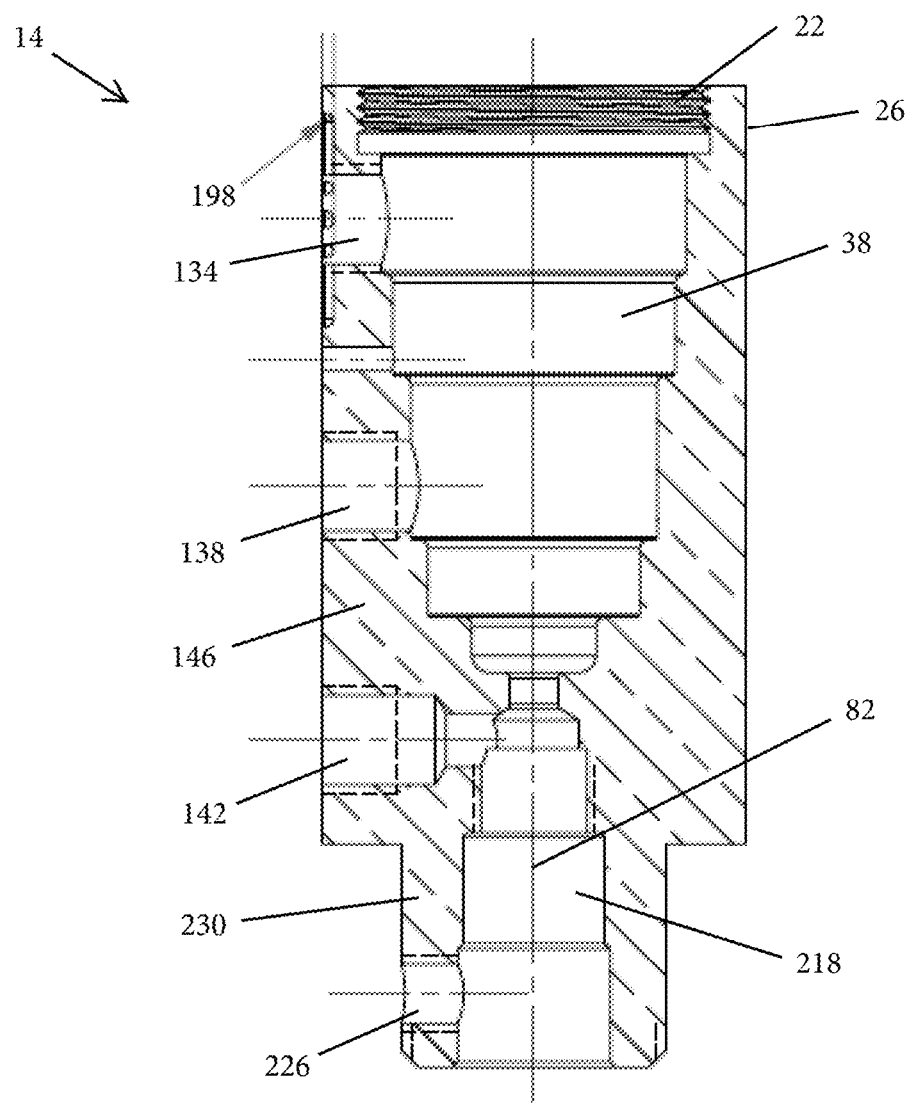
FIG. 3 is a cross-sectional view of the valve body.
Figure 4:
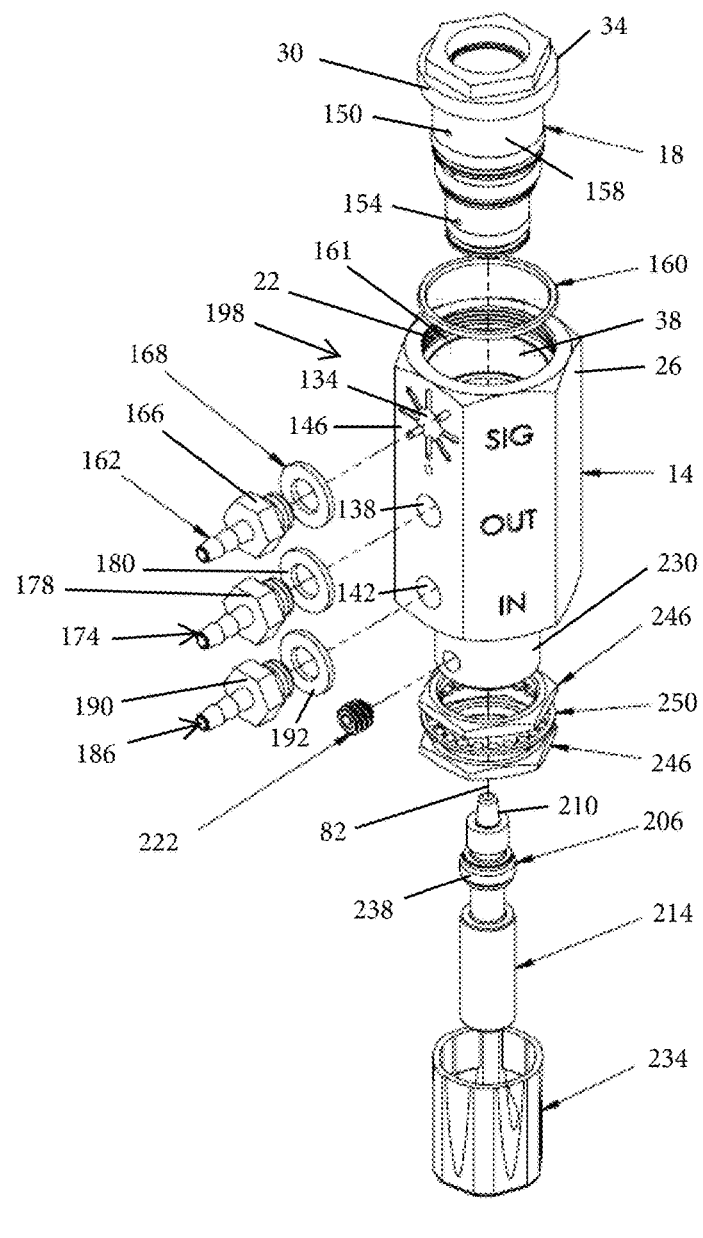
FIG. 4 is a perspective, partially exploded view of the water control valve, illustrating a plurality of air vent apertures on the valve body, and a needle.

With reference to FIGS. 3 and 4, the valve body 14 includes a first air inlet passageway 134, a first water outlet passageway 138, and a water inlet passageway 142. Each of the first air inlet passageway 134, the first water outlet passageway 138, and the water inlet passageway 142 extends through a wall 146 of the valve body 14. As illustrated in FIG. 3, the first air inlet passageway 134 and the first water outlet passageway 138 are in communication with the valve body internal cavity 38. In the illustrated construction, the first air inlet passageway 134, the first water outlet passageway 138, and the water inlet passageway 142 are all positioned along one side of the valve body 14, and are general aligned on top of one another. Other constructions include different arrangements than that illustrated.

With reference to FIGS. 1, 2, and 4, the valve cartridge 18 includes a second air inlet passageway 150 and a second water outlet passageway 154. Each of the second air inlet passageway 150 and the second water outlet passageway 154 extends through a wall 158 of the valve cartridge 18 and into the main cartridge body internal cavity 86. When the valve cartridge 18 is inserted into the valve body 14 and the internal threads 22 and the external threads 30 are engaged, the first air inlet passageway 134 aligns with the second air inlet passageway 150, and the first water outlet passageway 138 aligns with the second water outlet passageway 154.

With reference to FIGS. 4 and 5, the water control valve 10 further includes an eighth sealing member 160 that sits directly below the internal threads 22 on a ledge 161 within the valve body 14. When the valve cartridge 18 is inserted into the valve body 14, the valve cartridge 18 presses against the eighth sealing member 160 so as to seal the top end of the internal cavity 38 of the valve body 14 to the top end 34 of the valve cartridge 18.

With reference to FIGS. 4-7, the water control valve 10 further includes an air inlet port 162 that is removably coupled to the valve body 14. The air inlet port 162 directs air (or other gas) through the first air inlet passageway 134, into the second air inlet passageway 150, and into the main cartridge body internal cavity 86. In the illustrated construction the air inlet port 162 is an elongate, hollow, generally tubular structure having an enlarged threaded end 166 that presses against a washer 168 and threads onto a set of internal threads 170 (FIG. 5) in the wall 146 of the valve body 14. The air inlet port 162 is shaped to receive a hose or other air delivery structure. In some constructions, flow of air through the air inlet port 162 is controlled by a foot pedal or other device. Other constructions include different shapes and sizes for the air inlet port 162 than that shown.

With continued reference to FIGS. 4-7, the water control valve 10 further includes a water outlet port 174 that is removably coupled to the valve body 14. Water passes from the main cartridge body internal cavity 86, through the second water outlet passageway 154, through the first water outlet passageway 138, and into the water outlet port 174. In the illustrated construction the water outlet port 174 is an elongate, hollow, generally tubular structure having an enlarged threaded end 178 that presses against a washer 180 and threads onto a set of internal threads 182 (FIG. 5) in the wall 146 of the valve body 14. The water outlet port 174 is shaped to receive a hose or other water removal structure. Other constructions include different shapes and sizes for the water outlet port 174 than that shown.

With continued reference to FIGS. 4-7, the water control valve 10 further includes a water inlet port 186 that is removably coupled to the valve body 14. The water inlet port 186 directs water through the water inlet passageway 142. In the illustrated construction the water inlet port 186 is an elongate, hollow, generally tubular structure having an enlarged threaded end 190 that presses against a washer 192 and threads onto a set of internal threads 194 (FIG. 5) in the wall 146 of the valve body 14. The water inlet port 186 is shaped to receive a hose or other water delivery structure. Other constructions include different shapes and sizes for the water inlet port 186 than that shown.

Figure 4A:
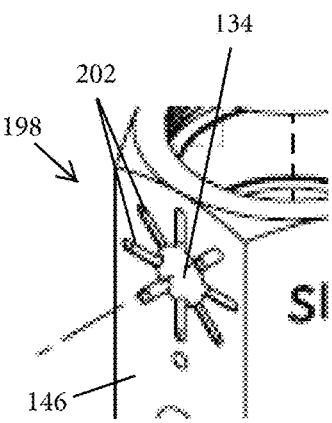
FIG. 4A is a partial, enlarged view of FIG. 4.

With reference to FIGS. 3-4A, the water control valve 10 further includes an air venting system 198. The air venting system 198 reduces or eliminates the noise of air leaving the first air inlet passageway 134, and also facilitates fast response times for closing of the water control valve 10. In the illustrated construction, the air venting system 198 includes a plurality of elongate grooves 202 (e.g., flutes or vanes) arranged concentrically around the first air inlet passageway 134 and disposed in the wall 146 (as seen in FIGS. 4 and 4A). Each of the elongate grooves 202 is in communication with the first air inlet passageway 134. In the illustrated construction eight grooves 202 are equally spaced around the first air inlet passageway 134, although in other constructions different numbers and arrangements of grooves 202 are provided. For example, in some constructions, four grooves 202 are provided. In some constructions two grooves 202 are provided. In some constructions the groove 202 or grooves 202 are not spaced evenly from one another, or are provided only along one side of the first air inlet passageway 134 instead of being spaced circumferentially around the first air inlet passageway 134. In the illustrated construction each of the elongate grooves 202 is linear and extends radially away from the first air inlet passageway 134. In other constructions one or more of the elongate grooves 202 also or alternatively extends circumferentially about the first air inlet passageway 134. In some constructions one or more of the elongate grooves 202 has a non-linear shape. In the illustrated construction each of the elongate grooves 202 has a rounded trough formed into the wall 146. In other constructions a square trough, or other-shape trough is formed into the wall 146. As illustrated in FIGS. 1 and 6, the air inlet port 162 covers portions of each of the elongate grooves 202, leaving radially distal ends 204 of the elongate grooves 202 exposed to an environment outside of the water control valve 10. When air is vented from the water control valve 10, the air flows radially outwardly along the elongate grooves 202 and then out of the water control valve 10 at these radially distal ends 204. In the illustrated construction, the total cross-sectional area of the elongate grooves 202 enables a large enough volume of venting air to pass out of the water control valve 10 so that the water control valve 10 has quick response times for closing of the water control valve 10, and so that there is a reduction or elimination of noise otherwise commonly associated with air venting.

With reference to FIG. 4, the water control valve 10 further includes an adjustable needle 206. The needle 206 includes a top end 210 and a bottom end 214. In the illustrated construction the needle 206 is generally tapered, such that the top end 210 has a smaller outside diameter than the bottom end 214. The needle 206 is adjustable up and down along the axis 82 to control a flow of water within the water control valve 10.

With reference to FIG. 3, the valve body 14 includes a needle cavity 218 to receive at least a portion of the needle 206. As illustrated in FIG. 3, the needle cavity 218 is in communication with valve body internal cavity 38, as well as with the water inlet passageway 142, and is tapered to generally match the taper of the needle 206.

With reference to FIG. 4, the water control valve 10 further includes a retaining member 222 that is used to lock movement of the needle 206 along the axis 82. In the illustrated construction the retaining member 222 is a set screw, although other constructions include different types of lock members, including other types of screws, bolts, rods, etc.

With reference to FIGS. 3-5, the water control valve 10 includes an adjustment passageway 226 in a bottom end 230 of the valve body 14 that receives and guides the retaining member 222. In the illustrated construction the adjustment passageway 226 is a threaded passageway that receives the retaining member 222, although in other constructions the adjustment passageway 226 is not threaded. As illustrated in FIG. 3, the adjustment passageway 226 extends through the wall 146 of the valve body 14 and is in communication with the needle cavity 218. The retaining member 222 may be moved along the adjustment passageway 226. When the retaining member 222 is moved far enough along the adjustment passageway 226, an end of the retaining member 222 abuts the needle 206 and retains a position of the needle 206 along the axis 82 (e.g., as a travel limiter as illustrated in FIG. 5). While only a single retaining member 222 and adjustment passageway 226 is illustrated, other constructions include different numbers and arrangements of lock members and adjustment passageways.

With reference to FIGS. 4 and 5, the water control valve 10 further includes a cap 234 that covers at least a portion of the needle 206. In the illustrated construction the cap 234 has a cup-like shape, such that the bottom end 214 of the needle 206 rests within an interior of the cap 234. Other constructions of the cap 234 include different shapes and sizes than that illustrated.

With continued reference to FIGS. 4 and 5, the water control valve 10 further includes a ninth sealing member 238, which is coupled to the needle 206. In the illustrated construction the ninth sealing member 238 is an O-ring, although other constructions include different types of sealing members. As illustrated in FIG. 5, the ninth sealing member 238 contacts an inner surface 242 of the wall 146 of the valve body 14 and prevents water from flowing down and out of the needle cavity 218 when the needle 206 is locked in position.

With continued reference to FIGS. 4 and 5, the water control valve 10 further includes retaining nuts 246 and a washer 250 that are movable up and down along the bottom end 230 of the valve body 14. In the illustrated construction the retaining nuts 246 are threaded nuts and the bottom end 230 of the valve body 14 has external threads (not shown) that engage the retaining nuts 246 to permit linearly movement of the retaining nuts 246 along the axis 82. As illustrated in FIG. 5, the retaining nuts 246 and washer 250 may be moved to a position where used for adjusting placement of the water control valve 10 within a mounting substrate (not shown).

FIGS. 5-7 illustrate use of the water control valve 10. With reference to FIG. 5, the water control valve 10 is in a static condition. In the static condition, water has been directed through the water inlet port 186, through the water inlet passageway 142, and into portions of both the needle cavity 218 and the valve body internal cavity 38, thereby surrounding the top end 210 of the needle 206, as well as the bottom end 78 of the piston 70. As described above, the ninth sealing member 238 prevents any of the water from moving down along the remainder of the needle 206. Additionally, the fourth sealing member 90, which is pressed against the main cartridge body 42, prevents any water from moving up further along the piston 70. In this static condition, the biasing member 130 is in an extended position, holding the top end 74 of the piston 70 up near, but still spaced from, the plug 102. As illustrated in FIG. 5, a gap 254 thus exists between the top end 74 of the piston 70 and the bottom end 110 of the plug 102.

With reference to FIGS. 4-6, the water control valve 10 is in an opening condition. In the opening condition, air has been directed from an air source through the air inlet port 162 (e.g., by depressing a foot pedal), through the first air inlet passageway 134, through the second air inlet passageway 150, and into the gap 254. The force of the air entering and filling the gap 254 forces the top end 74 of the piston 70 down against the biasing force of the biasing member 130, thereby compressing the biasing member 130 to a compressed position and expanding the gap 254 to be greater in size than in the static condition. As the piston 70 moves down along the axis 82, the bottom end 78 of the piston 70 and the fourth sealing member 90 move down as well away from the main cartridge body 42, thereby providing a pathway for water to move up into the main cartridge body 42. As illustrated in FIG. 6, this pathway allows the water to move through the second water outlet passageway 154 and the first water outlet passageway 138 and then out through the water outlet port 174, where the water may then be directed to a dental hand tool or other device, to a patient's mouth, or to anywhere else as desired. As illustrated in FIG. 6, the flow of water in the water control valve 10 is maintained separately from the flow of air within the water control valve 10. In some constructions, a quantity of air from the air supply used to direct air into the gap 254 is also directed to the dental hand tool or other device, so that a combination of air and water may be used in the dental hand tool or other device.

With continued reference to FIG. 6, the position of the needle 206 determines a flow rate of the water moving between the water inlet port 186 and the water outlet port 174. For example, if the needle 206 is moved down along the axis 82, the water flow rate will increase, whereas if the needle 206 is moved up along the axis 82, the water flow rate will decrease.

With continued reference to FIG. 6, in the opening condition the flow of air into the gap 254 may be more than needed to open the water control valve 10. In this case, the air venting system 198 permits some of the air to vent back out of the water control valve 10. In particular, and with reference to FIG. 3 as well, some of the air moves out of the first air inlet passageway 134 and flows out along the elongate grooves 202 and away from the water control valve 10. Use of the elongate grooves 202 allows the air to vent quickly when needed, thus providing quick response times for closing of the water control valve 10 (e.g., upward movement of the piston 70), as well as reducing or eliminating noise that might otherwise develop from release of air.

With reference to FIG. 7, the water control valve 10 is in a closing condition. In the closing condition, air is no longer flowing into the gap 254, but instead is flowing in a reverse direction back out of the gap 254 and through the air inlet port 162. Because of the lack of air entering the gap 254 due to the force of the biasing member 130, the gap 254 begins to decrease in size, allowing the piston 70 to move back up along the axis 82. Any excess air continues to be vented through the air venting system 198. As illustrated in FIG. 7, once the piston 70 has risen high enough along the axis 82, the fourth sealing member 90 again contacts and seals itself against the main cartridge body 42, thereby cutting off the flow of water to the water outlet port 174.

Variations and modifications exist within the scope and spirit of one or more independent aspects of the embodiments described.

Various embodiments, features, and advantages are set forth in the following claims.

What is claimed is:

1. A water control valve comprising:
   a valve body defining a valve body internal cavity, a first air inlet passageway in communication with the valve body internal cavity, a first water outlet passageway in communication with the valve body internal cavity, and a water inlet passageway, wherein the first air inlet passageway, the first water outlet passageway, and the water inlet passageway are each disposed along a same side of the valve body; and
   a valve cartridge removably coupled to the valve body, wherein the valve cartridge is sized to fit at least partially within the valve body internal cavity, the valve cartridge defining a second air inlet passageway and a second water outlet passageway;
   wherein the first air inlet passageway is aligned with the second air inlet passageway and the first water outlet passageway is aligned with the second water outlet passageway when the valve cartridge is coupled to the valve body;
   wherein the valve cartridge includes a piston and a spring coupled directly to the piston to bias the entire piston along an axis during operation of the water control valve, wherein the piston includes a top end configured to be pressed directly by air entering the valve cartridge through the second air inlet passageway, and a bottom end, wherein a sealing member is coupled adjacent the bottom end of the piston, wherein the valve cartridge is arranged such that when the spring is fully extended and the piston is fully biased along the axis, the water inlet passageway is sealed from the first water outlet passageway, and when the spring is compressed the water inlet passageway is in communication with the first water outlet passageway.

2. The water control valve of claim 1, wherein the valve cartridge includes a main cartridge body having a top end and a bottom end, and wherein an outside diameter of the main cartridge body tapers in a stepped manner moving from the top end toward the bottom end.

3. The water control valve of claim 1, wherein the valve cartridge includes a main cartridge body having a top end and a bottom end, the main cartridge body defining a main cartridge body internal cavity, wherein the piston and the spring are both disposed at least partially within the main cartridge body internal cavity.

4. The water control valve of claim 3, wherein the piston is movable from a first position where the bottom end of the piston and the sealing member prevent water from moving from the water inlet passageway to both the first and the second water outlet passageways, to a second position where water is free to move from the water inlet passageway to both the first and the second water outlet passageways.

5. The water control valve of claim 4, wherein the spring is a compression spring, and wherein the compression spring is in an extended position when the piston is in the first position, and wherein the compression spring is in a compressed position when the piston is in the second position.

6. The water control valve of claim 4, wherein the valve cartridge further includes a plug disposed at least partially within the main cartridge body internal cavity, wherein the plug includes a top end and a bottom end, wherein when the piston is in the first position, a gap exists between the top end of the piston and the bottom end of the plug, the gap having a first size, and wherein when the piston is in the second position, the gap has a second size greater than the first size.

7. The water control valve of claim 6, wherein the first air inlet passageway and the second air inlet passageway are each in communication with the gap, such that air introduced through the first air inlet passageway is configured to enter the gap and force the piston to move from the first position to the second position.

8. The water control valve of claim 1, wherein a flow of water in the water control valve is maintained separately from a flow of air within the water control valve.

9. The water control valve of claim 1, wherein the valve body includes a needle cavity in communication with the valve body internal cavity, and wherein the water control valve further includes a needle disposed at least partially within the needle cavity, the needle having a top end and a bottom end.

10. The water control valve of claim 9, wherein the valve body includes a top end and a bottom end, the bottom end of the valve body including an adjustment passageway, and wherein the water control valve includes a set screw that extends through the adjustment passageway and retains the needle along an axis, wherein the position of the needle along the axis determines a flow rate of water moving between the water inlet passageway and the first and the second water outlet passageways.

11. The water control valve of claim 1, wherein the first air inlet passageway, the first water outlet passageway, and the water inlet passageway are all positioned along one side of the valve body.

12. The water control valve of claim 1, wherein the valve body has a top end and a set of internal threads at the top end of the valve body, wherein the valve cartridge has a top end and a set of external threads at the top end of the valve cartridge.

13. A water control valve comprising:
a valve body defining a valve body internal cavity, a first air inlet passageway in communication with the valve body internal cavity, a first water outlet passageway in communication with the valve body internal cavity, and a water inlet passageway; and
a valve cartridge removably coupled to the valve body, wherein the valve cartridge is sized to fit at least partially within the valve body internal cavity, the valve cartridge defining a second air inlet passageway and a second water outlet passageway;
wherein the first air inlet passageway is aligned with the second air inlet passageway and the first water outlet passageway is aligned with the second water outlet passageway when the valve cartridge is coupled to the valve body;
wherein the valve cartridge includes a piston and a spring coupled directly to the piston to bias the entire piston along an axis during operation of the water control valve, wherein the piston includes a top end configured to be pressed directly by air entering the valve cartridge through the second air inlet passageway, and a bottom end, and wherein a sealing member is coupled adjacent the bottom end of the piston;
wherein the valve cartridge includes a main cartridge body having a top end and a bottom end, the main cartridge body defining a main cartridge body internal cavity, wherein the piston and the spring are both disposed at least partially within the main cartridge body internal cavity;
wherein the piston is movable from a first position where the bottom end of the piston and the sealing member prevent water from moving from the water inlet passageway to both the first and the second water outlet passageways, to a second position where water is free to move from the water inlet passageway to both the first and the second water outlet passageways; and
wherein the valve cartridge further includes a plug disposed at least partially within the main cartridge body internal cavity, wherein the plug includes a top end and a bottom end, wherein when the piston is in the first position, a gap exists between the top end of the piston and the bottom end of the plug, the gap having a first size, and wherein when the piston is in the second position, the gap has a second size greater than the first size.

14. The water control valve of claim 13, wherein the first air inlet passageway and the second air inlet passageway are each in communication with the gap, such that air introduced through the first air inlet passageway is configured to enter the gap and force the piston to move from the first position to the second position.

15. The water control valve of claim 13, wherein a flow of water in the water control valve is maintained separately from a flow of air within the water control valve.

16. The water control valve of claim 13, wherein the first air inlet passageway, the first water outlet passageway, and the water inlet passageway are all positioned along one side of the valve body.

17. A water control valve comprising:
a valve body defining a valve body internal cavity, a first air inlet passageway in communication with the valve body internal cavity, a first water outlet passageway in communication with the valve body internal cavity, and a water inlet passageway; and
a valve cartridge removably coupled to the valve body, wherein the valve cartridge is sized to fit at least partially within the valve body internal cavity, the valve cartridge defining a second air inlet passageway and a second water outlet passageway;
wherein the first air inlet passageway is aligned with the second air inlet passageway and the first water outlet passageway is aligned with the second water outlet passageway when the valve cartridge is coupled to the valve body;
wherein the valve cartridge includes a piston and a spring coupled directly to the piston to bias the entire piston along an axis during operation of the water control valve, wherein the piston includes a top end configured to be pressed directly by air entering the valve cartridge through the second air inlet passageway, and a bottom end, and wherein a sealing member is coupled adjacent the bottom end of the piston;
wherein the valve body includes a needle cavity in communication with the valve body internal cavity, and wherein the water control valve further includes a needle disposed at least partially within the needle cavity, the needle having a top end and a bottom end; and
wherein the valve body includes a top end and a bottom end, the bottom end of the valve body including an adjustment passageway, and wherein the water control valve includes a set screw that extends through the adjustment passageway and retains the needle along an axis, wherein the position of the needle along the axis determines a flow rate of water moving between the water inlet passageway and the first and the second water outlet passageways.

18. The water control valve of claim 17, wherein the valve cartridge includes a main cartridge body having a top end and a bottom end, and wherein an outside diameter of the main cartridge body tapers in a stepped manner moving from the top end toward the bottom end.

19. The water control valve of claim 17, wherein a flow of water in the water control valve is maintained separately from a flow of air within the water control valve.

20. The water control valve of claim 17, wherein the first air inlet passageway, the first water outlet passageway, and the water inlet passageway are all positioned along one side of the valve body.

* * * * *